(12) United States Patent
Giaever et al.

(10) Patent No.: US 7,399,631 B2
(45) Date of Patent: Jul. 15, 2008

(54) REAL-TIME IMPEDANCE ASSAY TO FOLLOW THE INVASIVE ACTIVITIES OF METASTATIC CELLS IN CULTURE

(75) Inventors: Ivar Giaever, Schenectady, NY (US); Charles R. Keese, Schoharie, NY (US)

(73) Assignee: Applied Biophysics, Inc., Troy, NY (US)

( * ) Notice: Subject to any disclaimer, the term of this patent is extended or adjusted under 35 U.S.C. 154(b) by 375 days.

(21) Appl. No.: 10/938,086

(22) Filed: Sep. 10, 2004

(65) Prior Publication Data

US 2005/0130119 A1 Jun. 16, 2005

Related U.S. Application Data

(60) Provisional application No. 60/501,714, filed on Sep. 10, 2003.

(51) Int. Cl.
*C12N 5/00* (2006.01)
*C12N 5/02* (2006.01)

(52) U.S. Cl. ..................................................... 435/325
(58) Field of Classification Search ....................... None
See application file for complete search history.

(56) References Cited

U.S. PATENT DOCUMENTS 5,187,096 A 2/1993 Giaever et al.

OTHER PUBLICATIONS

Morimoto et al. J of Investigative Surgery1993;6:25-32.*
Zak et al. Pflugers Arch-Eur J Physiol 2000;440:179-183.*
Smith et al. IEEE Transactions on Biomedical Engineering 2000;47:1403-1405.*
Zak et al. Eur J Physiol 2000;440:179-183.*
Depaola, N. et al., "Electrical Impedance of Cultured Endothelium Under Fluid Flow," Annals of Biomedical Engineering, vol. 29, pp. 1-9, 2001.

Wegener, J. et al., "Electric Cell-Substrate Impedance Sensing (ECIS) as a Noninvasive Means to Monitor the Kinetics of Cell Spreading to Artificial Surfaces," Experimental Cell Research 259, pp. 158-166, 2000.
Giaever, I. et al., "A Morphological Biosensor for Mammalian Cells," Nature, vol. 366, pp. 591-592, Dec. 9, 1993.
Giaever, I. et al., "Monitoring Fibroblast Behavior in Tissue Culture With an Applied Electric Field," Proc. Natl. Acad. Sci. USA, vol. 81, pp. 3761-3764, Jun. 1984.
Keese, CR et al., "A Biosensor that Monitors Cell Morphology with Electrical Fields," IEEE Engineering in Medicine and Biology, pp. 402-408, Jun./Jul. 1994.
Reddy, L. et al., "Assessment of Rapid Morphological Changes Associated with Elevated cAMP Levels in Human Orbital Fibroblasts," Experimental Cell Research 245, pp. 360-367, 1998.
Keese, CR. et al., "Cell-Substratum Interactions as a Predictor of Cytotoxicity," In Vitro & Molecular Toxicology, vol. 11, No. 2, pp. 183-192, 1998.
Giaever, I. et al., "Micromotion of Mammalian Cells Measured Electrically," Proc. Natl. Acad. Sci. USA, vol. 88, pp. 7896-7900, Sep. 1991.
Mitra, P. et al., "Electric Measurements Can be Used to Monitor the Attachment and Spreading of Cells in Tissue Culture," BioTechniques (The Journal of Laboratory Technology for Bio-research), vol. 11, No. 4, pp. 504-510, Oct. 1991.
Tiruppathi, C. et al., "Electrical Method for Detection of Endothelial Cell Shape Change in Real Time: Assessment of Endothelial Barrier Function," Proc. Natl. Acad. Sci. USA, vol. 89, pp. 7919-7923, Sep. 1992.
Keese, CR et al., "Real-Time Impedance Assay to Follow the Invasive Activities of Metastatic Cells in Culture," BioTechniques, vol. 33, No. 4, pp. 842-850, 2002.

* cited by examiner

*Primary Examiner*—Jon P Weber
*Assistant Examiner*—Bin Shen
(74) *Attorney, Agent, or Firm*—Hoffman Warnick LLC (57) ABSTRACT

The present invention provides methods for the assessment of the metastatic potential of cells by measuring the effect of the cells on the impedance of an electrode. Accordingly, the present invention similarly provides methods for establishing indicators of metastatic potential based on a cell's effect on impedance. Such methods may be employed in vitro or in vivo. In some embodiments, the electrode is coated with endothelial or epithelial cells.

9 Claims, 6 Drawing Sheets

Figure 1. ECIS measurements of HUVEC inoculations. Measurements made in seven individual wells were at 4 kHz, and the resistive portion of the impedance is presented. All electrodes were precoated with gelatin.

Figure 2. Effect of adsorbed gelatin coatings on HUVEC behavior. Measurements of the resistive portion of the impedance at 4 kHz are shown following inoculation at time zero. Duplicate inoculations were made in wells having electrodes without special pretreatment and in wells where electrodes were precoated with adsorbed gelatin. This striking influence of substrate coating was observed for some lots of HUVECs; however, many lots showed a much less pronounced effect. The lower trace is of a well not receiving cells.

Figure 3. Resistance changes during MLL cell challenges. Resistance changes in the impedance at 4 kHz as confluent layers of HUVEC cells are challenged with MLL Dunning cell suspensions in the presence of 10% and 1% FBS in the media. The control curve received medium without cells.

Figure 4. Normalized resistance changes during Dunning subline challenges. Normalized resistance changes in the impedance at 4 kHz as confluent layers of HUVECs are challenged with suspensions of (upper panel) the G and AT3 Dunning sublines and (lower panel) the G, AT1, and AT2 Dunning sublines (resistance is normalized to its starting value, approximately 10 000 $\Omega$).

Figure 5. Resistance changes during MLL cell or conditioned medium challenges. Resistance changes in the impedance at 4 kHz, as confluent layers of HUVECs are challenged with MLL cell suspension and MLL-conditioned medium.

Figure 6. Normalized resistance changes during live or dead cell challenges. Challenge of HUVEC layers with both live and heat-killed MLL cells and with live G cells. The resistive portion of the impedance at 4 kHz is normalized to its starting value (approximately 2000 Ω without cells and 12 000 Ω for the four traces of confluent HUVEC layers).

Figure 7. Changes in model parameters during AT3 cell challenge. A challenge of a confluent HUVEC layer showing the time course of resistance changes and changes in parameters based on a model of cell-induced impedance changes.

Figure 8. Prostatic cell challenge. HUVECs were challenged with several different human prostatic cell suspensions. The resistive portion of the impedance normalized to its value at time zero is presented.

REAL-TIME IMPEDANCE ASSAY TO FOLLOW THE INVASIVE ACTIVITIES OF METASTATIC CELLS IN CULTURE

CROSS-REFERENCE TO RELATED APPLICATIONS

The current application claims the benefit of co-pending U.S. Provisional Application No. 60/501,714 filed Sep. 10, 2003, which is hereby incorporated herein by reference.

BACKGROUND OF THE INVENTION (1) Technical Field

The present invention relates generally to the field of cellular monitoring and more specifically to methods for assessing cellular metastatic potential through impedance monitoring.

(2) Related Art

The growth of large solid tumors is dependent on an aberrant cell exhibiting uncontrolled proliferation and expressing the genes required to recruit endothelial cells to undergo angiogenesis, allowing the mass to grow beyond the constraints of passive diffusion (10). Notwithstanding, these behaviors alone do not result in multiple tumor formation—the hallmark of most malignant cancers. For secondary tumor formation via a blood-borne route, some tumor cells leave the primary mass, disrupt the basement membrane of capillary endothelial cells, affect the retraction of the endothelial cells, move through the intercellular junctions, and enter the circulatory system. After moving some distance from the primary tumor, these cell then attach to or become arrested near distant endothelial cells, traverse the spaces between these cells, disrupt the basement membrane structure, and migrate into the underlying tissue (4). Uncontrolled proliferation again ensues to form a new secondary tumor. As these activities are repeated, multiple tumors are established and, if unheeded, ultimately result in the death of the organism.

This complex in vivo metastatic behavior involves the regulation and expression of many genes involved in such diverse activities as endothelial cell binding (14), cell signaling resulting in endothelial retraction (11), the synthesis and secretion of proteolytic enzymes (1), and cell locomotion (3). These various activities can be isolated and individually observed in vitro. In addition, these components can be collectively studied using tissue culture methods similar to those introduced by Kramer and Nicolson (13). Here, a cell monolayer of bovine endothelial cells was first established and then exposed to cell suspensions of a variety of both tumorigenic and nontumorigenic cells.

Cell behavior was studied using scanning and transmission electron microscopy as well as phase-contrast timelapse microscopy. When endothelial cell monolayer were challenged with highly metastatic cell lines, such as the B16 melanoma cells, observations were recorded that showed the binding of the cells to the endothelial cell layer, the retraction of the endothelial cell junctions, and finally, the penetration of the cells through the endothelial monolayer.

This in vitro sequence of activities has been suggested to represent similar invasive activities that take place during the metastatic process in vivo. The assay provides striking images of the behavior of the metastatic cell but, by nature, is difficult to quantify and cannot provide information in real time regarding the dynamics of the process. Since its introduction, this type of assay has been modified and used extensively to monitor transendothelial migration of tumor cells in vitro. Although many of these approaches have involved qualitative microscopic observations, others have employed radio or fluorescent labeling of the tumor cells to yield quantitative measurements. Such labeling, however, often utilizes hazardous probes or requires the use of specialized equipment in order to produce quantitative data. A need exists, therefore, for a safe and simple quantitative method of assessing metastatic cellular behavior.

Such a quantitative method is the electric cell-substrate impedance sensing (ECIS™, Applied BioPhysics, Troy, N.Y., USA) method first described by Giaever and Keese (6) in 1984. Since then, the method has been used to provide information regarding real-time changes in cell morphology, including cell substrate interactions, cell motility, and cell layer barrier function (7-9, 12, 15, 16, 18, 19).

The purpose of the research leading to the present invention was to determine the efficacy of such an ECIS™-based assay in assessing the metastatic potential of a cell. Concomitant methods would include, for example, methods for testing the efficacy of anti-cancer therapies and methods for establishing indicators of metastatic potential.

SUMMARY OF THE INVENTION

The present invention provides methods for the assessment of the metastatic potential of cells by measuring the effect of the cells on the impedance of an electrode. Accordingly, the present invention similarly provides methods for testing the efficacy of anti-cancer therapies and for establishing indicators of metastatic potential based on a cell's effect on impedance. Such methods may be employed in vitro or in vivo. In some embodiments, the electrode is coated with endothelial or epithelial cells.

A first aspect of the invention provides a method of assessing a metastatic potential of a cell comprising the steps of providing an electrode coated with a plurality of substrate cells, obtaining a first measurement of at least one electrical property of the coated electrode, contacting the electrode with at least one test cell, obtaining a second measurement of at least one electrical property of the coated electrode, and comparing the first and second measurements.

A second aspect of the invention provides a method of assessing the efficacy of an anti-cancer therapy comprising the steps of assessing a first metastatic potential of a test cell, providing an anti-cancer therapy to the test cell, assessing a second metastatic potential of the test cell, and comparing the first and second metastatic potentials.

A third aspect of the invention provides a method of developing an indicator of metastatic potential comprising the steps of providing a plurality of sets of index cells of known metastatic potentials, providing an electrode coated with a plurality of substrate cells, obtaining a first measurement of at least one electrical property of the coated electrode, contacting the electrode with a first set of index cells, obtaining a second measurement of at least one electrical property of the coated electrode, repeating the contacting step and the obtaining a second measurement step for each of the sets of index cells, and comparing the first and second measurements for each of the sets of index cells to the known metastatic potential of each of the sets of index cells, wherein the difference in the first and second measurements is predictive of metastatic potential.

The foregoing and other features of the invention will be apparent from the following more particular description of embodiments of the invention.

BRIEF DESCRIPTION OF THE DRAWINGS

The embodiments of this invention will be described in detail, with reference to the following figures, wherein like designations denote like elements, and wherein.

DETAILED DESCRIPTION OF THE INVENTION

Electric impedance assays are used to determine the cancerous potential of cells, i.e., the potential of cells to grow and propagate without natural inhibition. In particular, the invention is useful to determine the metastatic potential of cells. The cells can be derived from any animal including humans and other mammals. Cells may be obtained, for example, by biopsy. Alternatively, samples of cells taken from a body can be propagated ex vivo prior to use in the invention. Cells may be in a dispersion or suspension or they may still be in tissue.

In a preferred embodiment, the cells that are being tested are contacted with an electrode that has previously been coated with a cell substrate. Any of a number of electrodes and counter electrodes can be used depending upon, e.g., the current to be applied and the configuration of the apparatus in which the assay is carried out. Typically, an alternating current (ac) of about 0.01 to about 100 microamperes (μA), more typically, about 0.1 to about 10 μA, e.g., about 1.0 μA, is applied at a frequency of about 0.01 to about 100 kilohertz (kHz), more typically, about 0.1 to about 40 kHz, e.g., about 4.0 kHz.

An apparatus for carrying out the method of the invention can take any of multiple forms. In one embodiment, the electrode is placed at or near the bottom surface of a planar material upon which cells can be grown. For example, gold film surface electrodes, approximately 100 to 1000 microns in diameter, are positioned in the bottoms of multiple wells in a multi-well plate, with one or more larger counter electrodes positioned to be in contact with a liquid medium in which the cells to be tested, e.g., Dulbecco's Modified Eagle's medium with 10% fetal bovine serum, are cultured. The electrode may or may not cover the entire surface area of the bottom of each well. The electrodes and counter electrode are "joined" by a culture medium that is capable of transferring current across the electrode and the counter electrode.

In a preferred embodiment, the electrode is coated with a cell substrate and the cancerous potential of test cells is determined by observing the change in impedance of the cell substrate. The cells that form the cell substrate are preferably endothelial cells, i.e., cells that line the surfaces of, e.g., the circulatory and lymphatic systems, but other cells, e.g., epithelial cells, can also be used. Illustrative cell types include, e.g., HUVEC (Human Umbilical Vein Endothethial cells), HPMEC (Human Pulmonary Microvascular Endothelial Cells), BAEC (Bovine aortic endothelial cells), or epithelial cells such as MDCK, BS-C-1. In preferred embodiments, the cells that form the substrate are typically grown to confluence on or closely adjacent the electrode. The electrode can be coated with a protein or other macromolecular layer that enhances cell growth and adhesion on the electrode. By way of illustration, 1 mg/mL gelatin in 0.15M NaCl can be used to form an adsorbed layer of gelatin.

After the cells in the cell substrate have grown to confluence, the impedance will rise to a level characteristic of the cell type and fluctuations in impedance should reach a steady state. The cell substrate can then be contacted with the cells to be tested and the change in impedance measured as the cells to be tested are cultured. The cells to be assessed are generally cultured in contact with the coated electrode for up to about 10 to about 100 hours. The cells to be tested can be tested at the same time and even in the same apparatus as, but in different compartments from, control cells, e.g., cells known to be non-cancerous and non-metastatic. Cells that are normal, cells that are cancerous or potentially cancerous (i.e., likely to become cancerous), and cancer cells that are metastatic or potentially metastatic (i.e., likely to become metastatic) will have differing effects on the impedance of the electrode.

It is also possible to measure the cancerous and/or metastatic potential of cells without use of a cell substrate. In such an embodiment, a sample of the cells to be tested is cultured directly on the electrode and impedance changes are observed in substantially the same way. Preferably, impedance changes resulting from propagation of the cells to be tested are compared to the impedance changes caused by control cells.

A useful apparatus is the ECIS™ device manufactured by Applied BioPhysics, Troy, N.Y., USA. This device is described in the company website, www.biophysics.com, the entire content of which is incorporated herein by reference as though fully set forth. Useful apparatuses and process conditions are also taught by U.S. Pat. No. 5,187,096 to Giaever et al., which is also incorporated by reference herein as though fully set forth.

It is also possible to observe impedance changes under fluid flow conditions. In this embodiment, the liquid culture medium is caused to flow over the cell substrate, if any, and the test cells to produce a shear stress that approximates the laminar shear stress to which the cells are exposed in their natural environment, i.e., in the body of the animal from which they were removed. For a description of illustrative means of carrying out the invention under flow conditions, see, e.g., DePaola et al. (2), which is incorporated by reference herein as though fully set forth.

To determine the cancerous or metastatic state or potential of the cells to be assessed, the change in impedance caused by the test cells is compared to the change caused by a control cell or cells. The control cells can be normal cells or cells with a characterized cancerous or metastatic state or potential. Alternatively, it will be apparent that the change in impedance can be assigned a value based on a previously calibrated scale, such scale having been generated through prior experiments with multiple index cells. Using such a scale, the cells to be assessed can be assigned an objectively generated score, which score will indicate the relative cancerous or metastatic state or potential.

Thus, another embodiment of the invention is a method of developing an indicator of a cancerous or metastatic state or potential that comprises contacting multiple preparations of an electrode coated with a cell substrate with different lots of cells wherein each lot has a known cancerous or metastatic state or potential, measuring the effect of each lot of cancerous cells on electrical impedance, and determining a quantitative or qualitative measure of metastatic potential for each lot of cancerous cells, wherein the measure reflects the actual or a relative effect on impedance and whereby such measure is the indicator of a cancerous or metastatic state or potential.

A related aspect of the invention is a method of determining responsiveness of transformed cells to anti-cancer therapies which comprises determining the metastic potential of the cancerous cells prior to, during, or after treatment by measuring and comparing the effect of samples of the cells on impedance by a cell-substrate prior to, during, or after treatment, whereby reduction in the degree of lessening of impedance indicates that the cells are responsive to the treatment. Such treatments include, for example, chemical treatments and radiological treatments.

For example, cells taken by biopsy can be cultured ex vivo in multiple units. Each unit can be treated with a different chemotherapeutic agent. While the cells are undergoing such ex vivo treatment, and/or after the cells have been so treated, they can be cultured on an electrode, e.g., an electrode coated with a cell substrate, and their effects on impedance can be measured relative to each other or to untreated cells. In this way, the relative effects of different therapeutic regimens can be tested and the treatment thereby optimized for a particular patient or type of cancer.

The example that follows is illustrative and not limiting of the invention.

EXAMPLE

A. Materials and Methods

1. ECIS™

The ECIS™ Model 100 and an earlier prototype version of the instrument were used for this work. To study cell behavior with this instrument, cells are grown in culture wells containing gold film surface electrodes. Normal culture medium serves as the electrolyte. An approximate constant current source applies an ac signal of 1 µA, usually at 4 kHz, between a small active electrode (250-micron diameter) and a large counter electrode to complete the circuit. Voltage is monitored with a lock-in amplifier providing amplitude and phase data. In addition to reporting impedance, these data are also converted to resistance or capacitance, treating the cell electrode system as a simple resistor and capacitor in series. As the cells attach and spread upon the small electrode, they constrict the current, forcing it to flow beneath and between the cells, resulting in large increases in impedance. The microampere currents and the resulting voltage drop of a few millivolts have no measurable effect on the cells, and hence, the monitoring of cell behavior is noninvasive (5).

2. Cell Culture Procedures

The Johns Hopkins Brady Urological Institute supplied the Dunning sublines in frozen ampoules. These were thawed and grown in RPMI 1640 medium (Invitrogen, Carlsbad, Calif., USA) supplemented with 2 mM L-glutamine and containing 10% FBS with 250 nM dexamethasone and 50 µg/mL gentamicin in a 5% CO2, 37° C., high-humidity atmosphere. The behavior of the various lines had been previously studied (3). The specific Dunning lines used in this work included the highly metastatic ML, MLL, and AT3 sublines; the weakly metastatic AT1 and AT2 sublines; and the essentially non-metastatic G subline. Passaging was with trypsin/EDTA, and frozen stocks were prepared using standard procedures with medium containing 10% DMSO and 20% FBS.

Human prostatic cell lines (DU145, PC3, TSU, and PPC1) were also obtained from Johns Hopkins and handled in an identical manner. For ECIS™ studies, cells were taken from slightly subconfluent cultures 48 hours after passage and a monodisperse cell suspension was prepared using standard tissue culture techniques with trypsin/EDTA. These suspensions were equilibrated at incubator conditions before addition to the electrode-containing wells.

Human umbilical vein endothelial cells (HUVECs) and their growth medium were purchased from VEC Technologies (Rensselaer, N.Y., USA). Medium 199 contained 80 µg/mL heparin, endothelial growth factor, 10% FBS, and 50 µg/mL gentamicin. Passaging was with trypsin/EDTA and frozen stocks were prepared as described above. Endothelial cells were generally passaged 6-8 times, and then the stock of cells was replaced.

3. Preparation and Initial Inoculation of Electrodes with HUVEC Suspensions

Electrode arrays were supplied by Applied BioPhysics, where the goldfilm electrodes were fabricated using photolithographic techniques on Lexan® polycarbonate supports. These were connected to the electronics as previously described (19). The completed arrays consisted of eight individual small electrodes (250-µm diameter) with larger counter electrodes located at the base of small wells (approximately 600 µL volume with 0.8 $cm^2$ substrate area) for cell culture. Each well was normally used with 400 or 450 µL medium.

For most experiments, gelatin was used to precoat the ECIS™ wells by flooding the bottom of each well with a solution of 200 µg/mL gelatin in 0.15 M NaCl. After a 15-minute incubation to allow the gelatin to adsorb, the protein solutions were aspirated and the electrode-containing wells were rinsed twice. They were then partially filled with 200 µL HUVEC medium and allowed to equilibrate in the tissue culture incubator for 15-60 minutes.

A HUVEC suspension was prepared at $5\times10^5$ cells/mL and 200 µL were added to each well, resulting in a final surface concentration of $1.25\times10^5$ cells/$cm^2$ and a well volume of 400 µL. Following inoculation of cells into ECIS™ wells, the attachment and spreading were followed by impedance measurements. The HUVECs were generally incubated for 1-2 days before the prostatic cell challenge. Impedance measurements were used to verify that confluence was achieved and maintained and that the cells exhibited normal levels of impedance fluctuations, indicative of healthy cell layers (15).

4. Challenge of Endothelial Layers

The Dunning cells were cultured to near confluence with regular feedings of RPMI medium. Monodisperse cell suspensions were prepared in fresh Medium 199 (HUVEC medium) at $20\times10^5$ cells/mL, and 50 µL were added to wells containing endothelial cell monolayers (450 µL total well volume). This resulted in a final surface concentration of Dunning cells of $1.25\times10^5$ cells/$cm^2$ (one Dunning cell for each endothelial cell). The impedance of the challenged endothelial cell layer was monitored via ECIS™ for the next 12-20 hours. Sometimes, following the measurement, the medium was aspirated and the cells were fixed with 10% formalin and stained with methylene blue. Identical procedures were used for the human lines.

5. Conditioned Dunning Medium

Medium used to maintain confluent cultures of Dunning cells for 72 hours was removed from culture vessels and centrifuged at 3000 g for 10 minutes to remove any suspended cells. This medium was then used to replace 250 μL medium removed from an ECIS™ well with a confluent HUVEC layer in place.

B. Results and Discussion

Figure 1:
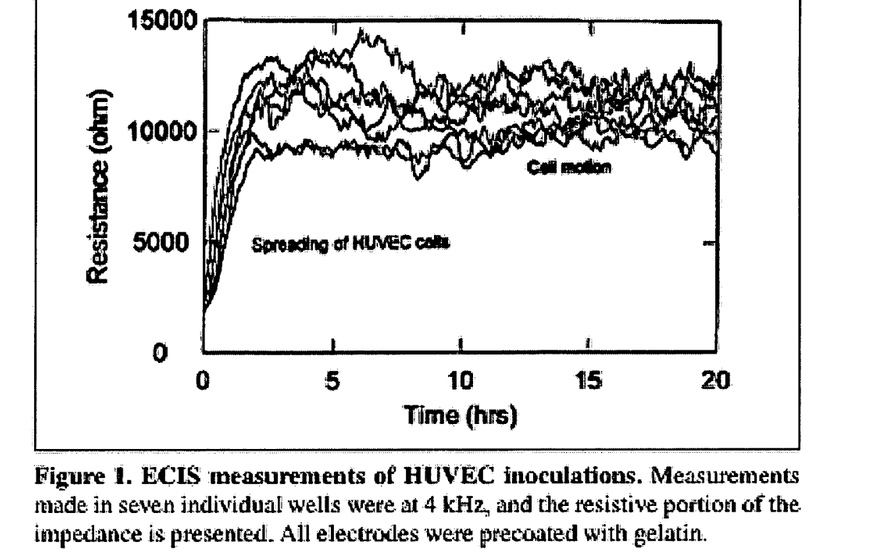
FIG. 1 shows ECIS™ impedance measurements of electrodes coated with human umbilical vein endothelial cells (HUVEC).

FIG. 1 shows the initial attachment of the HUVECs measured via time-course impedance changes. Seven individual electrodes are followed from the time of inoculation (time zero) to 20 hours after inoculation. The initial rise in the curve is due to cell attachment and spreading that, for this lot of HUVECs, increased the resistive portion of the impedance at 4 kHz from six to seven times that of the cell-free electrode.

Figure 2:
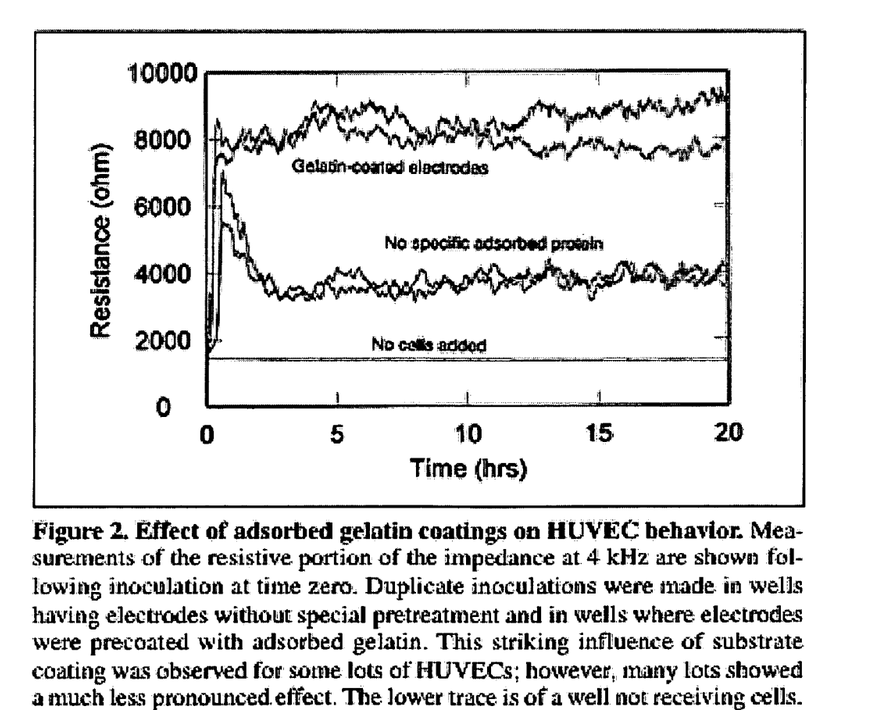
FIG. 2 shows ECIS™ impedance measurements of electrodes both uncoated and coated with adsorbed gelatin.

Spreading is completed in approximately 2.5 hours. The resistance fluctuations result from movement or undulations of the established cell sheet that constrain the current. These changes are both due to fluctuations in the transcellular barrier function and in the spacing between the basal side of the cell and the electrode surface (8). A second endothelial cell attachment curve using a different lot of HUVECs is shown in FIG. 2 for four inoculated electrodes and also one control electrode that receives no cells. In these data, there is a difference in the behavior of the HUVECs on electrodes precoated with adsorbed gelatin compared to those where the adsorbed protein layer is simply a collection of those proteins found in the FBS used to supplement the growth medium. This response to gelatin-coated substrates was seen only for some specific lots of HUVEC tested. Nevertheless, as a tight layer (high impedance) was deemed best considering the nature of the experiments, in most work reported, the electrodes were precoated with gelatin.

Figure 3:
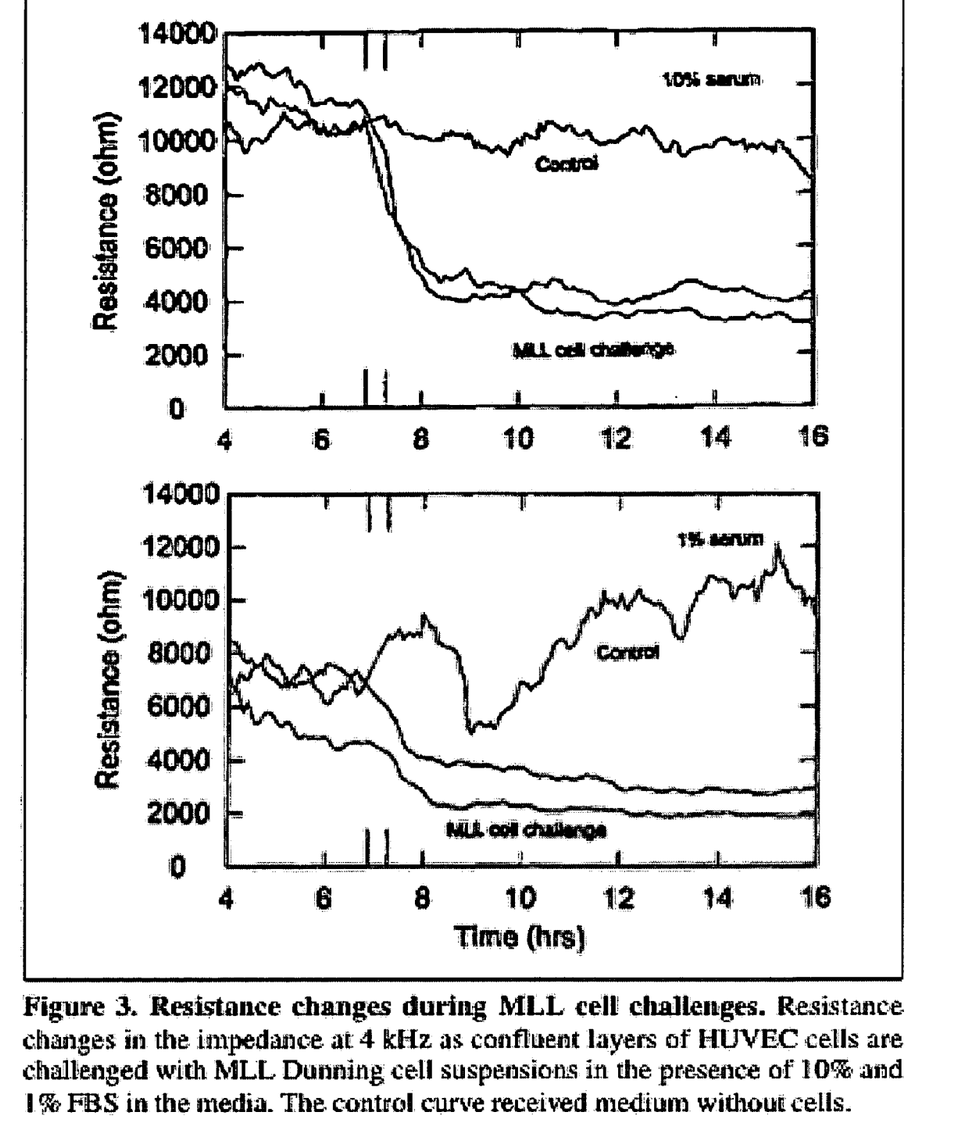
FIG. 3 shows ECIS™ impedance measurements of HUVEC-coated electrodes challenged with MLL Dunning cell suspensions.

FIG. 3 (upper panel) is the first of several figures showing changes in the resistive portion of the impedance during the challenge of the endothelial cell layer, in this case with the highly metastatic Dunning MLL cells. The experimental curve is run in duplicate with complete medium containing 10% FBS as described in the experimental methods.

Data acquisition began at time zero (not shown) when the HUVEC layer was established and completely confluent. Impedance data recording is briefly paused at the first vertical mark on the horizontal axis. MLL cells (50 μL suspension) are then added, and at the second vertical mark (around 7.2 hours) data acquisition resumes. Time measurement continues during this pause, and the resistance recorded at the start and end of the pause are connected with a straight line. The control curve received a sham at this time and is essentially unaffected by the addition of 50 μL fresh Medium 199 without cells. There is a substantial drop in the resistance of the wells exposed to the MLL cells over an approximately 2-hour period. These changes are presumably due to direct interactions of the metastatic cells and endothelial monolayer, resulting first in retraction of the endothelial cell junctions, followed by extravasation of the metastatic cells to the substratum. After this drop, the sustained reduced resistance is that of the collection of HUVEC and MLL cells on the substratum. Microscopic examination of fixed and stained preparations of the cells a few hours after the challenge revealed a disorderly layer with some open areas and a considerable number of partially spread and rounded cells.

We were curious whether the withdrawal of serum from the medium would alter the system's response, as serum components might play a role in either promoting the metastatic cell activities or in stabilizing the endothelial cell layer. In the lower panel of FIG. 3, an experiment shows the ability of the assay to function at reduced serum concentration. In this experiment, HUVECs were inoculated and grown for two days in standard medium containing 10% FBS. The confluent layer was then allowed to equilibrate in medium with only 1% FBS for several hours before the addition of the sham or the MLL cells in Medium 199 now with 1% FBS. As can be seen upon comparing these two figures, the lower serum concentration has resulted in a noticeable drop in the intact HUVEC layer resistance, from around 12,000 at 10% FBS to about 7,000 at the 1% level. Nevertheless, there is a substantial further drop elicited by the MLL cell suspension addition, as well as a quieting of the typical endothelial cell impedance fluctuations. Again, the sham has little effect on the control curve. The ability to work at low serum concentration or in defined medium could also prove useful in reducing or eliminating the interference of serum components in future mechanistic studies.

Figure 4:
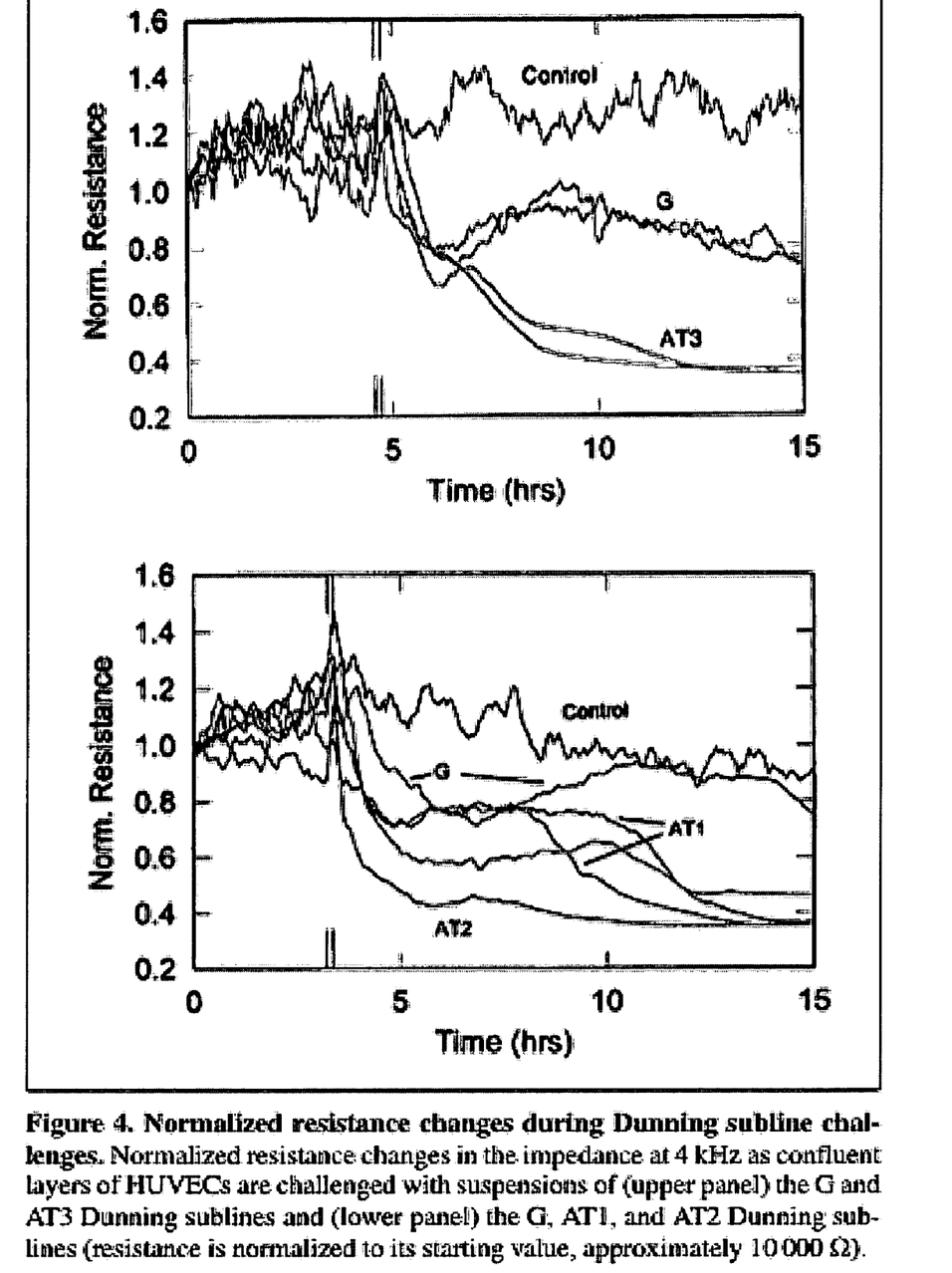
FIG. 4 shows normalized resistance ECIS™ impedance measurements of HUVEC-coated electrodes challenged with Dunning subline suspensions.

FIG. 4 shows varying effects of different sublines of the Dunning series using this challenge assay. These data are normalized by dividing the resistive portion of the impedance by its value at time zero for each well (approximately 10,000), providing an easy comparison of the fractional change in resistance. In the upper and lower panels of FIG. 4, HUVEC layers are challenged with Dunning cells added in 50 μL complete Medium 199 containing $20 \times 10^5$ cells/mL. The vertical lines are the same as in FIG. 3, and a sham is added to the control curve. In the upper panel of FIG. 4, duplicate wells received the weakly metastatic G subline and the highly metastatic AT3 subline. The G cell addition, unlike the previous MLL additions, brings about a smaller initial drop in resistance, and the resistance of the collection of cells undergoes partial reversal in this drop and displays some return of cell-induced impedance fluctuations. The AT3 challenge, although resulting in a less steep drop in impedance than MLL, results in curves eventually reaching resistance levels near that of cell-free electrodes and with nearly complete elimination of detectable cell motion (resistance fluctuations). The ML highly metastatic subline had behavior similar to that of MLL (data not shown). In the lower panel of FIG. 4, three different Dunning strains are used, namely G, AT1, and AT2. In this run, the two electrodes with AT2 cells elicit a slightly more rapid drop in the resistance than do the electrodes with AT1 cells, although both sublines reportedly have similar metastatic potential in vivo. With the exception of the lowest AT2 trace, these show impedance changes that are intermediate between the G subline and the highly metastatic lines. The G cells again show the rebound pointed out in the upper panel of FIG. 4.

Metalloproteinases and other soluble factors are known to play a role in the metastatic process. Work with murine sarcoma cells (20) and human pancreatic cancer cells (17) had shown that medium conditioned by the cancer cell lines induced endothelial cell retraction. Experiments were carried out to determine if the possible addition of soluble factors released by the metastatic cells would have an effect on the impedance of the HUVEC layer similar to that observed with the cell suspensions. These effects could not be observed under the conditions of our studies.

Figure 5:
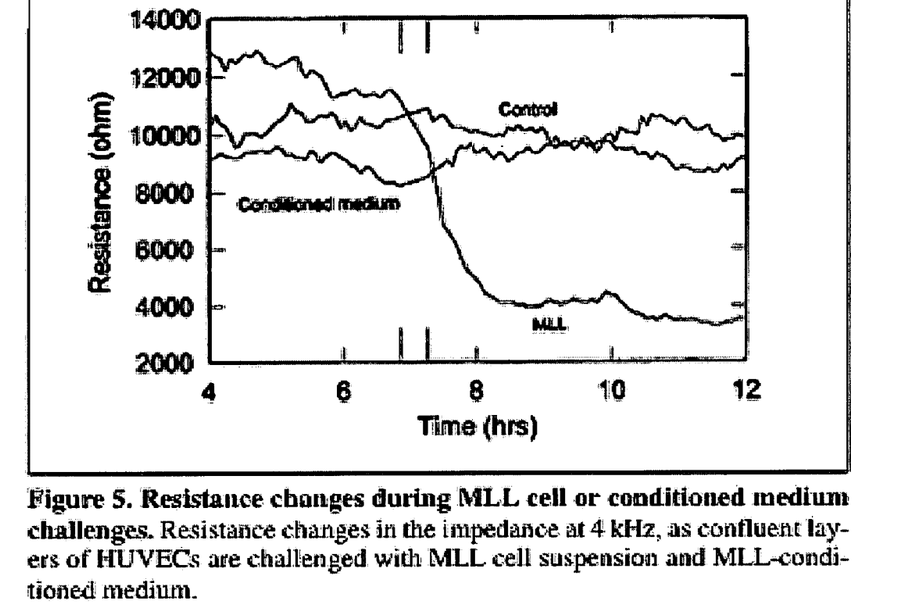
FIG. 5 shows ECIS™ impedance measurements of HUVEC-coated electrodes challenged with MLL cell suspension and MML-conditioned medium.

FIG. 5 shows the ECIS™ response of HUVECs exposed to conditioned medium as well as whole cells. MLL cells added in 50 μL fresh medium bring about the clear drop in resistance. The control curve in this case had 250 μL medium replaced with fresh medium (total volume 400 μL), whereas the other trace had 250 μL medium replaced with medium that was conditioned for three days by highly confluent MLL cultures.

Figure 6:
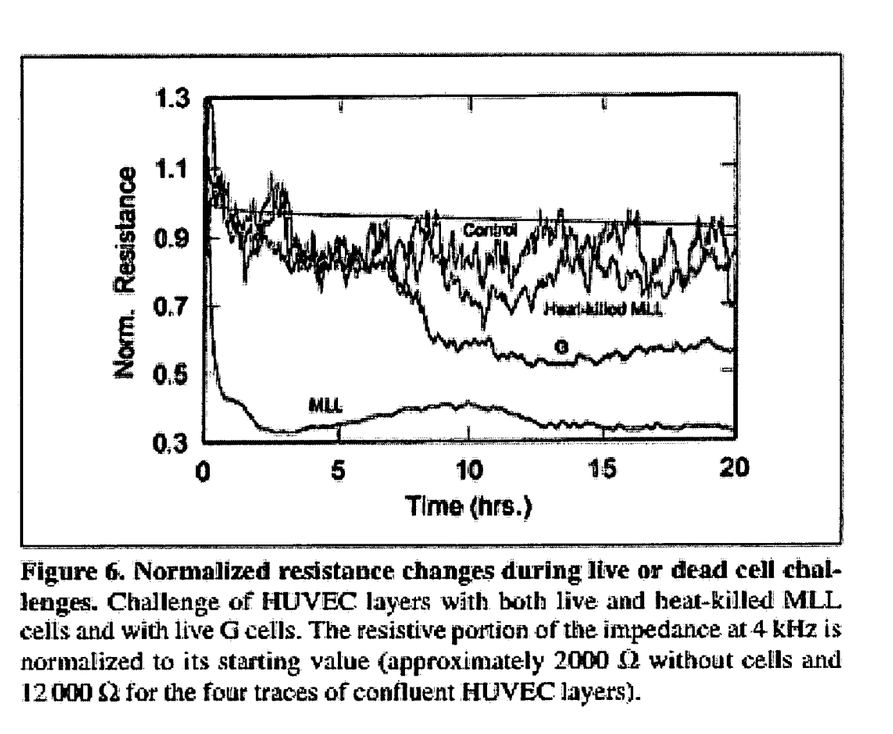
FIG. 6 shows ECIS™ impedance measurements of HUVEC-coated electrodes challenged with live and heat-killed MLL cells and live G cells.

Since large numbers of cells are being added during the challenge, we investigated the possibility that a reaction to the crowded conditions or contact with the cell membranes simply caused the HUVEC cells layer to be altered. To accomplish this, MLL cells were heat killed by exposure to 55° C. for 15 minutes before addition to the established HUVEC culture. The results of this experiment are shown in FIG. 6, where four traces are shown where established endothelial layers are exposed to cell suspensions or a sham at time zero and the normalized resistance is plotted against time. Here we see the normal response of the HUVECs to healthy MLL and the G cell sublines, but the medium sham (control) and the heat-killed cell additions elicit no response and are indistinguishable in FIG. 6. The fifth straightline trace is the normalized resistance measured from a well without cells. The slight drift in this curve is due to evaporation from the well and the resulting decrease in the resistivity of the medium.

Figure 7:
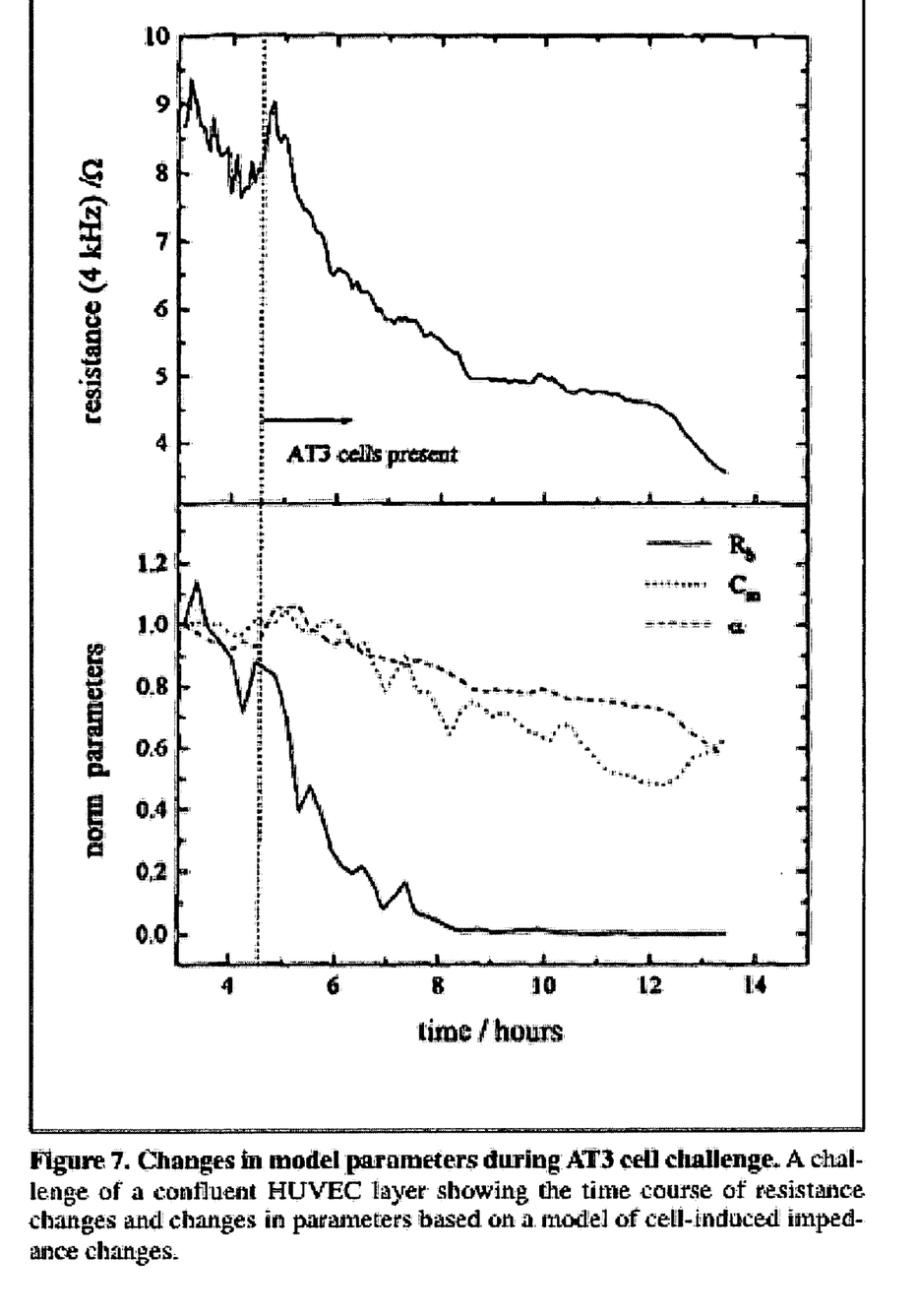
FIG. 7 shows ECIS™ impedance measurements of HUVEC-coated electrodes challenged with AT3 cells.

Using a published model of the cell electrode interaction (8), we have further analyzed the metastatic response to examine the behavioral changes taking place. The model was developed to calculate the specific impedance of a cell covered electrode ($Z_c$) as a function of the applied ac frequency (f). In the model, cells are treated as circular disks of radius $r_c$ and hovering a distance, h, over the electrode surface and bathed in medium of resistivity ρ. The specific impedance of the cell-free electrode ($Z_n$) is assumed to remain constant and is experimentally measured. $Z_m$ is the impedance to ac current flow directly through the two plasma membranes due to membrane capacitance, $C_m$. In the model, the extracellular current flows radially in the spaces formed between the ventral surface of the cell and the electrode surface before exiting to solution through transcellular spaces.

Solution of the equations associated with the model gives the specific impedance of the cell-covered electrode as:

$$\frac{1}{Z_c} = \frac{1}{Z_n}\left[\frac{Z_n}{Z_n + Z_m} + \frac{\frac{Z_m}{Z_n + Z_m}}{\frac{\gamma r_c}{2} \cdot \frac{I_0(\gamma r_c)}{I_1(\gamma r_c)} + R_b\left(\frac{1}{Z_n} + \frac{1}{Z_m}\right)}\right]$$

where $I_0$ and $I_1$ are modified Bessel functions of the first kind of order 0 and 1.

This solution depends on three parameters: $R_b$, the resistance between the cells for a unit area α, defined by:

$$\gamma r_c = r_c \sqrt{\frac{\rho}{h}\left(\frac{1}{Z_n} + \frac{1}{Z_m}\right)} = \alpha \sqrt{\frac{1}{Z_n} + \frac{1}{Z_m}} \cdot C_m$$

where $C_m = -i/(\pi f Z_m)$.

Time-course data of a HUVEC-AT3 challenge were measured at three different ac frequencies (400, 4,000, and 40,000 Hz). The time points were then fitted using the model. Reasonable values of the three parameters are first chosen and then used to calculate values of $Z_c$ and the corresponding values of the series resistance and capacitance at the three measuring frequencies. The calculated and experimental values are then compared and the model parameters altered to improve the fit. This is continued in an iterative process until an acceptable fit is obtained. These parameters are then used as starting values for analysis of the second time point in the series and so on. FIG. 7 shows the raw data in the upper panel and the calculated changes in the three model parameters in the lower panel. Notice that most of the change associated with the metastatic cell challenge is in the parameter $R_b$, the barrier function of the layer. This is presumably due to the retraction of the HUVECs from one another, opening up intercellular spaces for less obstructed current flow.

Some of the basic challenge experiments were also performed using a base layer of MDCK epithelial cells (data not shown). Although this base layer usually produced results similar to those described above with HUVECs, considerable variation was found from experiment to experiment. We believe this variation can be attributed to the very high barrier function of MDCK monolayers that can be an order of magnitude higher than that of the endothelial cells. A similar size retraction of the cell intercellular spaces will result in a considerably larger percentage drop in impedance for the MDCK than for the HUVEC layer. This very high sensitivity to the challenge could reflect subtle variations in experimental conditions not seen with the HUVEC layers. Another epithelial cell line, BSC-1, essentially did not respond to the metastatic cell challenge. This lack of response could be biological in nature—a failure of cell-cell interactions to result in the behavior observed with HUVECs. It is also possible that the weaker barrier function of the BSC-1 cells diminishes the ECIS™ response to the retraction of the intercellular spaces as described above. Although HUVEC cultures are more demanding in their culture requirements, these monolayers both responded strongly to the metastatic cells and gave results that were consistent from experiment to experiment.

Figure 8:
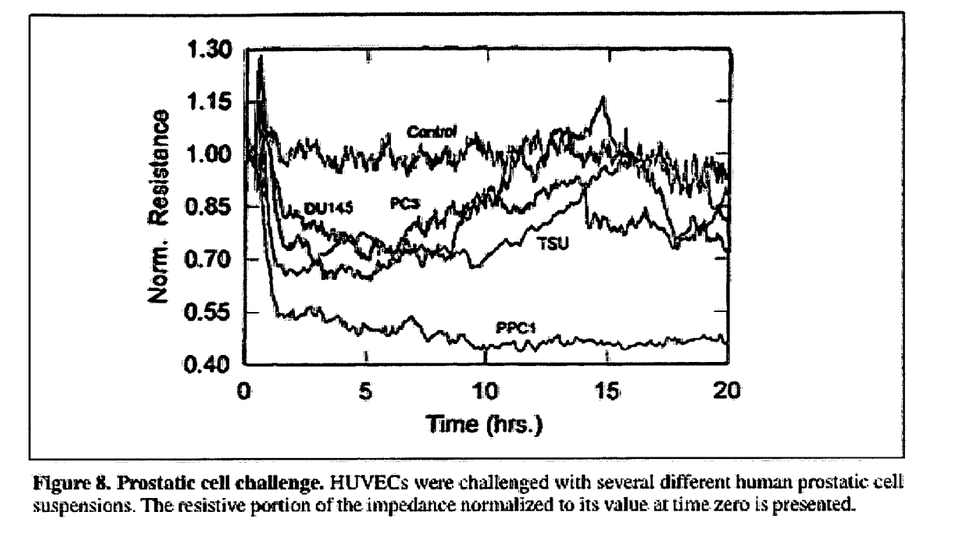
FIG. 8 shows ECIS™ impedance measurements of HUVEC-coated electrodes challenged with human prostatic cell suspensions.

We have carried out challenges with several human prostatic cancer cell lines. Results of confluent HUVEC monolayers challenged with $10^5$ cells/$cm^2$ DU154, PC3, PPC1, and TSU lines are shown in FIG. 8. The PPC 1 line clearly results in the most rapid and complete disruption of the endothelial cell layer. The other lines seem fairly similar, but one can discern possible differences in the slope and size of the initial drop, the degree of fluctuations in the signals, and the final impedance level obtained. We hope in the future to determine if these more subtle observations are reproducible and if they can be related to the in vivo behavior of the lines.

The ECIS™ instrumentation is now being adapted to monitor the activities of endothelial cells under both laminar and turbulent flow (2). It will be of interest to see if the behaviors described above are altered under these conditions encountered during the metastatic process in vivo.

The following references are referred to above and are incorporated herein as though fully set forth.

1. Brooks, P. C., S. Stromblad, L. C. Sanders, T. L. von-Schalscha, R. T. Aimes, W. G. Stetler-Stevenson, J. P. Quigley, and D. A. Cheresh. 1996. Localization of matrix metalloproteinase MMP-2 to the surface of invasive cells by interaction with integrin alpha v beta 3. Cell 85:683-693.
2. DePaola, N., J. E. Phelps, L. Florez, C. R. Keese, F. L. Minnear, I. Giaever, and P. I. Vincent. 2001. Electrical impedance of cultured endothelium under fluid glow. Ann. Biomed. Eng. 29:1-9.
3. Epner, D. E., A. W. Partin, J. A. Schalkan, J. T. Isaacs, and D. S. Coffey. 1993. Association of glyceraldehyde-3-phosphate dehydrogenase expression with cell motility and metastatic potential of rat prostatic adenocarcinoma. Cancer Res. 53:1995-1997.
4. Fidler, I. J. and R. Radinsky. 1990. Genetic control of cancer metastasis. J. Natl. Cancer Inst. 82:166-168.
5. Ghosh, P. M., C. R. Keese, and I. Giaever. 1994. Morphological response of mammalian cells to pulsed ac fields. Bioelectrochem. Bioenergetics 33:121-133.

6. Giaever, I. and C. R. Keese. 1984. Monitoring fibroblast behavior with an applied electric field. Proc. Natl. Acad. Sci. USA 81:3761-3764.
7. Giaever, I. and C. R. Keese. 1986. Use of electric fields to monitor the dynamical aspect of cell behavior in tissue culture. IEEE Trans. Biomed. Eng. 33:242-247.
8. Giaever, I. and C. R. Keese. 1991. Micromotion of mammalian cells measured electrically. Proc. Natl. Acad. Sci. USA 88:7896-7900. (Erratum 90:1634.)
9. Giaever, I. and C. R. Keese. 1993. A morphological biosensor for mammalian cells. Nature 366:591-592.
10. Hahnfeldt, P., D. Panigrahy, J. Folkman, and L. Hlatky. 1991. Tumor development under angiogenic signaling: a dynamical theory of tumor growth, post-vascular dormancy and treatment response. Cancer Res. 59:4770-4775.
11. Honn, K. V., D. G. Tang, I. Grossi, Z. M. Duniec, J. Timar, C. Renaud, M. Leithauser, I. Blair, et al. 1994. Tumor cell derived 12(S)-hydroxyeicosatetraenoic acid induces microvascular endothelial-cell retraction. Cancer Res. 54:565-574.
12. Keese, C. R., N. Karra, B. Dillon, A. Goldberg, and I. Giaever. 1998. Cell-substratum interactions as a predictor of vytotoxicity. In Vitro Toxicol. 11:83-192.
13. Kramer, R. H. and G. L. Nicolson. 1979. Interactions of tumor cells with vascular endothelial cell monolayers: a model for metastatic invasion. Proc. Natl. Acad. Sci. USA 76:5704-5708.
14. Lafrenie, R. M., T. J. Podoe, M. R. Buchanan, and F. W. Orr. 1992. Up-regulated biosynthesis and expression of endothelialcell vitronectin receptor enhances cancer celladhesion. Cancer Res. 52:2202-2208.
15. Lo, C. M., C. R. Keese, and I. Giaever. 1993. Monitoring motion of confluent cells in tissue culture. Exp. Cell Res. 204:102-109.
16. Mitra, P., C. R. Keese, and I. Giaever. 1991. Electric measurements can be used to monitor the attachment and spreading of cells in tissue culture. BioTechniques 11:504-511.
17. Okamoto, H., S. Nakamori, M. Mukai, K. Shinkai, H. Ohigashi, O. Ishikawa, H. Furukawa, S. Imaoka, et al. 1998. Down-regulation of focal adhesion kinase, pp125 (FAK), in endothelial cell retraction during tumor cell invasion. Clin. Exp. Metastasis 16:243-252.
18. Tiruppathi, C., A. B. Malik, P. J. Del Vecchio, C. R. Keese, and I. Giaever. 1992. Electrical method for detection of endothelial cell shape change in real time. Proc. Natl. Acad. Sci. USA 89:7919-7923.
19. Wegener, J., C. R. Keese, and I. Giaever. 2000. Electric cell-substrate impedance sensing (ECIS) as a noninvasive means to monitor the kinetics of cell spreading to artificial surfaces. Exp. Cell Res. 259:158-166.
20. Yasuda, T., H. Matsui, M. Kanamori, K. Yudoh, K. Ohmori, M. Aoki, and H. Tsuji. 1999. Effects of tumor cell-derived interleukin 1 alpha on invasiveness of metastatic clones of murine RCT sarcoma through endothelial cells. Tumor Biol. 20:105-116.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A method of assessing a metastatic potential of a cell comprising the steps of:
    providing an electrode coated with a plurality of substrate cells selected from at least one of endothelial and epithelial cells;
    obtaining a first measurement of at least one electrical property of the coated electrode; contacting the electrode with at least one test cell;
    obtaining a second measurement of at least one electrical property of the coated electrode;
    comparing the first and second measurements: and
    concluding, in the case that the second measurement is consistent with a decrease in impedance relative to the first measurement, that the at least one test cell is potentially metastatic.

2. The method of claim 1, wherein the electrical property is impedance.

3. The method of claim 2, wherein the test cell is considered potentially metastatic if the second measurement of impedance is less than the first measurement of impedance.

4. The method of claim 1, wherein the test cell is contacted in vivo.

5. The method of claim 1, wherein at least one of the obtaining and contacting steps are carried out under flow conditions.

6. The method of claim 1, further comprising the step of comparing the first and second measurements to a first and a second measurement of an electrical property of a cell known to be non-metastatic.

7. A method of developing an indicator of metastatic potential comprising the steps of:
    providing a plurality of sets of index cells of known metastatic potentials;
    providing an electrode coated with a plurality of substrate cells selected from at least one of endothelial and epithelial cells;
    obtaining a first measurement of at least one electrical property of the coated electrode;
    contacting the electrode with a first set of index cells;
    obtaining a second measurement of at least one electrical property of the coated electrode;
    repeating the contacting step and the obtaining a second measurement step for each of the sets of index cells; and
    comparing the first and second measurements for each of the sets of index cells to the known metastatic potential of each of the sets of index cells, wherein the difference in the first and second measurements is predictive of metastatic potential.

8. The method of claim 7, wherein the electrical property is impedance.

9. The method of claim 7, wherein at least one of the obtaining and contacting steps are carried out under flow conditions.

* * * * *